United States Patent
Berretta

[19]

[11] Patent Number: 6,158,272

[45] Date of Patent: Dec. 12, 2000

[54] TESTER FOR STRUCTURAL INTEGRITY OF BUILDING MATERIALS AND METHOD

[76] Inventor: Dominic Berretta, 4749 Bowen Rd., Memphis, Tenn. 38122

[21] Appl. No.: 09/274,701

[22] Filed: Mar. 23, 1999

[51] Int. Cl.[7] ............................................... G01N 3/48
[52] U.S. Cl. ............................................................. 73/82
[58] Field of Search ........................... 73/81–83, 12.09, 73/12.12, 821, 82

[56] References Cited

U.S. PATENT DOCUMENTS

| | | | |
|---|---|---|---|
| 880,991 | 3/1908 | Von Hassel . | |
| 1,942,982 | 1/1934 | Schneider | 265/18 |
| 2,522,544 | 9/1950 | Seyboth | 73/102 |
| 2,656,716 | 10/1953 | Hoggatt | 73/81 |
| 3,498,120 | 3/1970 | MacMillan | 73/102 |
| 3,999,424 | 12/1976 | Saint-Remy Pellissier | 73/81 |
| 5,176,026 | 1/1993 | Leeb et al. | 73/79 |
| 5,792,960 | 8/1998 | Lewis et al. | 73/81 |

FOREIGN PATENT DOCUMENTS

| | | | |
|---|---|---|---|
| 1769075 | 10/1992 | U.S.S.R. | 73/81 |

OTHER PUBLICATIONS

Charles Askew, Tennessee Association of Realtors, *Report to the Tennessee Association of Realtors from its Presidential Advisory Group on Synthetic Stucco Concerns and the Seller's or Buyer's Broker* (Aug. 15, 1997).

Ron McClure, *Open Letter to EIFS Home Owners* (date unknown).

Legal Notice, *Ruff et al. v. Parex et al*, No. 96–CVS–0059 (N.C. Super. Ct., New Hanover City, N.C.) (May 6, 1998).

David Mildenberg, *Some Homes Rotting Behind Synthetic Stucco* (Nov. 24, 1995).

J.W. Taylor, III, Taylor Ter–ro Exterminating Co., Inc., *Letter to Customers* (date unknown).

Home Base News, *Report on Moisture Problems Related to Exterior Insulation Finish Systems* (Jan. 1996).

Masonry Advisory Council, *Trendy Stucco Comes Unstuck!* (1993).

Paul Nordman, State Auto Insurance Company, *Exterior Finishing Insulation Systems* (Apr. 9, 1997).

James Overstreet, *Synthetic Stucco Opponents Form Memphis Chapter*, Memphis Business Journal (Aug. 1997).

*Primary Examiner*—Robert Raevis
*Attorney, Agent, or Firm*—Walker, McKenzie & Walker, PC

[57] ABSTRACT

A method and apparatus for testing structural integrity of a building material. Examples are given for testing the structural integrity of substrate behind synthetic stucco and stucco. The tester has an exposed elongated pointed tip that reciprocates within a casing that is electrically insulated from the pointed tip for safety. The pointed tip has a pointed end with an inclusive angle of sixty degrees. A spring forcibly opposes movement of the pointed tip into the casing, and a scale on the casing shows the maximum force exerted by the spring to the pointed tip. As the pointed tip is pushed through Exterior Insulation and Finish System ("EIFS") synthetic stucco to the substrate sheathing therebehind, an indicator shows the force applied by the pointed tip to the substrate sheathing. Substrate sheathing with acceptable structural integrity will withstand a force greater than a certain calibrated minimum, while substrate sheathing that lacks acceptable structural integrity will not withstand such a certain minimum calibrated force. The method of the present invention uses the tester of the present invention to test the structural integrity of a building material such as, for example, the substrate behind EIFS synthetic stucco.

3 Claims, 2 Drawing Sheets

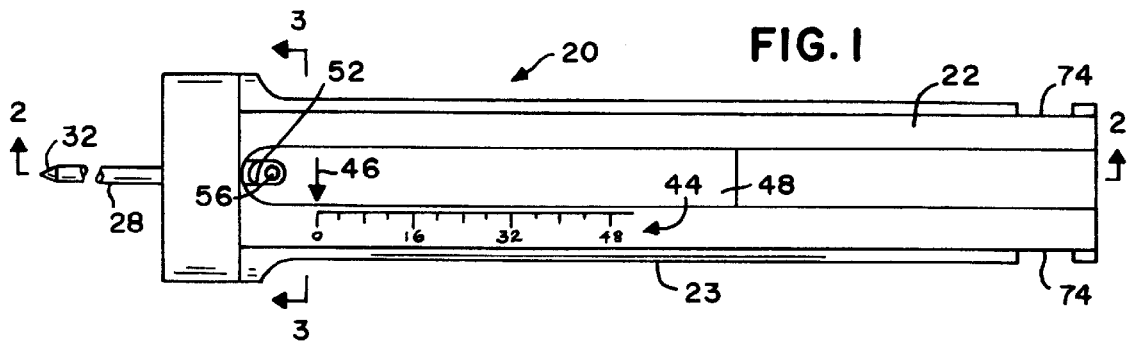
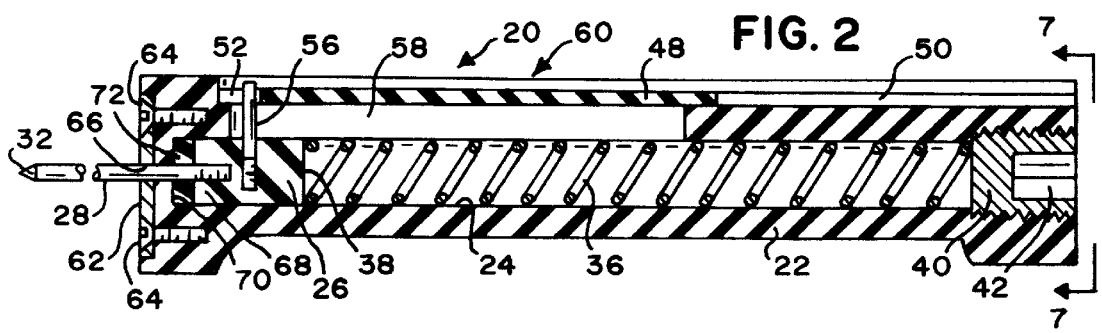
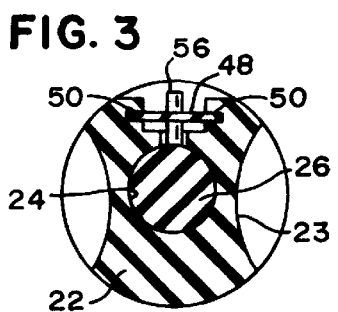
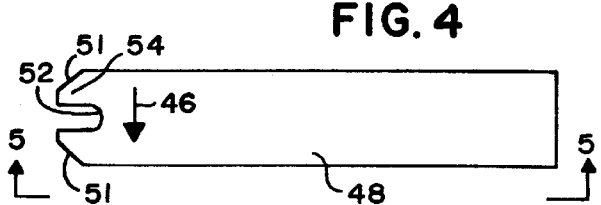
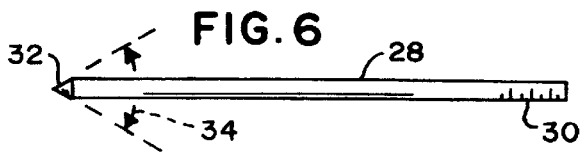
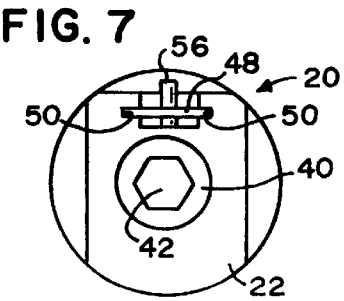

TESTER FOR STRUCTURAL INTEGRITY OF BUILDING MATERIALS AND METHOD

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO A "MICROFICHE APPENDIX"

Not applicable.

BACKGROUND OF THE INVENTION

1. Field of the Invention

The present invention relates, in general, to methods and apparatus for testing the structural integrity of building materials such as exterior siding, sheathing, and framing on buildings, such as might be found, for example, underneath synthetic stucco and stucco.

2. Description of the Prior Art

There are three major types of stucco-type exteriors for buildings, namely, "job-mixed" stucco, "mill-mixed" stucco, and synthetic stucco.

So-called job-mixed or "traditional" stucco is a mixture of portland cement, hydrate lime, aggregate (usually sand), and water, mixed in a manner and in proportions well-known to those skilled in the art. This stucco mixture is applied to a metal lath base attached to the outside of a substrate on the exterior of a building, and the stucco covers and is embedded within the lath. The substrate should be or have a moisture barrier in order to keep water drainage from entering the underlying substrate structure. A first or "scratch" coating of the stucco mixture is applied to embed the lath and then a second coating of the stucco mixture is applied to bring the stucco thickness to approximately 0.75 inch (1.9 cm), the minimum acceptable standard. Additives for the stucco mixture are available to provide a third and final coating with a variety of textures and colors. Also, elastomeric or acrylic coatings may be used for the final coat.

So-called mill-mixed stucco consists of the same basic materials as does job-mixed stucco, except that some manufacturers add chemical plasticizers to enhance the workability of the stucco and also may add fibers to provide additional strength to the finished stucco. The lath system for mill-mixed stucco is basically the same as for job-mixed stucco, but accessory trim pieces will typically be designed for the required depth of the applied mill-mixed stucco. A texture coat is often applied as a second coat to the mill-mixed stucco, but texture and color can also be provided by the application of a third stucco coat, as with the job-mixed stucco.

Synthetic stucco, otherwise known an Exterior Insulation and Finish System ("EIFS"), is a barrier-type cladding system that relies entirely on the exterior surface to keep moisture out of the cladding. Because there is no internal drainage system, the design and quality of workmanship is an important component in ensuring a water-tight finish. There are two variants of EIFS synthetic stucco systems, namely, EIFS Polymer Based and EIFS Polymer Modified.

EIFS Polymer Based ("EIFS PB") stucco systems, commonly referred to as the "soft system", is more soft and flexible due to a higher resin content. The system is adhesively and/or mechanically attached to the substrate, and has been commonly used for the last ten years in the Mid-South region of the United States. The expanded polystyrene ("EPS") base of the EIFS PB stucco system is a minimum of 0.75 inch (1.9 cm.) thick, and the EPS board is usually attached to the structural sheathing using a polymer-modified cement or an emulsion-type cement that does not attack the EPS board. In some instances, large (usually plastic) washers are nailed or screwed through the EPS board to provide additional or primary attachment of the EPS board to the substrate or frame. After allowing time to cure, usually 24 hours, fiberglass mesh is embedded into a layer of polymer-modified cement troweled over the EPS board. This troweled cement layer must dry before the finish coat can be applied (usually, another 24 hours). The finish coat is, most often, an elastomeric or acrylic containing color and an aggregate of the type required to obtain a desired texture. The EIFS PB synthetic stucco system is a single barrier, water exclusion, system. Most manufacturers have tested their lamina for water penetration, and most are water tight. However, a water vapor can pass through, thereby allowing the system to ventilate. Because this system is a single-barrier system, when or if water infiltrates through an unsealed area, the water is trapped until it vaporizes. If this condition persists, and the source of water intrusion is not stopped, then structural damage can occur. In response to the water infiltration problems with the EIFS PB synthetic stucco system, most manufacturers have designed a moisture management system ("PBMM"), whose purpose is to release any trapped water down a drainage plane between the sheathing and the EPS board.

EIFS Polymer Modified synthetic stucco systems, commonly referred to as the "hard system", is a cross from mill-mixed stucco and the EIFS PB moisture management system. The EIFS Polymer Modified synthetic stucco system does not provide a drainage plane and the wall has a hard base and finish coat. This system can often be installed over EPS board or an extruded polystyrene sheet.

The sheathing substrate most commonly used behind BIFS systems are exterior gypsum board, oriented strand board ("OSB"), and 0.5 inch (1.27 cm) CDX plywood. Other substrates are approved but not often used.

Because of excessive water intrusion and retention within its barriers, EIFS synthetic stucco systems have produced internal wall damage and rot to the underlying dwelling structure. There is uncertainty among those skilled in the art as to whether these problems stem from improper installation of the EIFS product or instead from a defect relating to or inherent in the product itself. Some manufacturers of EIFS have changed their product specifications in an attempt to reduce these problems.

As installed EIFS ages, excessive water intrusion may result from improper maintenance of the necessary seals around the points of water entry (e.g., window frames, doors, etc.) and from punctures in the exterior of the EIFS. Subsequent home improvement projects and repair of punctures in the EIFS exterior by uninformed workmen may result in inadequate seals that lead to excessive water intrusion and resulting rotting of the underlying sheathing substrate.

In an EIFS-covered wall, excessive water retention and internal wall damage may have no visible signs and may be undetectable by typically knowledgeable persons. Similarly, it is difficult to evaluate dwellings for suspected termite damage behind an EIFS synthetic stucco exterior. Prior art methods of testing for sheathing rot damage under an EIFS-covered wall required drilling and cutting of the EIFS covering so that moisture probes could be inserted to test for moisture, or else the EIFS covering would be partially or completely removed for inspection, and removal of the EIFS exterior is believed to be the only known prior art method of evaluating the underlying wood structures for termite damage. A typical and well-known moisture probe often used in such testing is the Delmhorst moisture meter model BD-8 or BD-9 using model 21E moisture probe electrodes. Such prior art methods of testing were intrusive and destructive of the EIFS covering, often resulting in great unnecessary expense to the dwelling's owner.

Additionally, prior art testing using moisture probes is successful in identifying trapped moisture under the EIFS covering, but did not directly test the structural integrity of the underlying substrate for rot. The focus of the prior art testing methods was to identify the presence of rot-causing moisture so that the source of the moisture could be addressed. However, in those situations where moisture had been present in the past but was no longer present, the prior art methods of testing could indicate satisfactory EIFS conditions because of the lack of moisture when, in fact, prior significant rot damage to the underlying substrate had occurred.

Therefore, a method and apparatus for testing the structural integrity of building materials such as a building's sheathing and framing is needed that can test for rotting and termite-damaged substrate sheathing such as might be found behind synthetic stucco without requiring removal of synthetic stucco or stucco outer layers.

BRIEF SUMMARY OF THE INVENTION

The present invention is a method and apparatus for testing structural integrity of building materials such as a building's sheathing and framing. The testing of sheathing and framing behind synthetic stucco is used as an example of the applicability of the present invention. The testing apparatus of the present invention has an exposed elongated pointed tip that reciprocates within a casing that is electrically insulated from the pointed tip for safety. A spring forcibly opposes movement of the pointed tip into the casing, and a scale on the casing shows the maximum force exerted by the spring to the pointed tip. As the pointed tip is pushed through the building materials such as, for example, the substrate sheathing and framing behind EIFS synthetic stucco or stucco, an indicator shows the force applied by the pointed tip to the substrate sheathing. Substrate sheathing with acceptable structural integrity will withstand a force greater than a certain calibrated minimum, while substrate sheathing that lacks acceptable structural integrity will not withstand such a certain minimum calibrated force.

The method of the present invention uses the tester of the present invention to test the structural integrity building materials such as, for example, substrate sheathing and framing behind EIFS synthetic stucco or stucco, in the manner hereinbefore described.

It is an object of the present invention to provide a tester and method for testing for structural integrity of building materials such as, for example, sheathing and framing behind EIFS synthetic stucco or stucco, without having to completely remove the synthetic stucco or stucco from the underlying substrate.

BRIEF DESCRIPTION OF THE SEVERAL VIEWS OF THE DRAWING

FIG. 1 is a top view of the tester of the present invention.

FIG. 2 is a longitudinal side sectional view of the present invention, taken substantially along the line 2—2 shown in FIG. 1.

FIG. 3 is a transverse sectional view of the present invention, taken substantially along the line 3—3 shown in FIG. 1.

FIG. 4 is a top plan view of the scale of the present invention.

FIG. 5 is a side view of the scale of the present invention, taken substantially along the line 5—5 shown in FIG. 4.

FIG. 6 is a side view of the cylindrically-symmetric pointed tip of the present invention.

FIG. 7 is a rear view of the present invention, taken substantially along the line 7—7 shown in FIG. 2.

DETAILED DESCRIPTION OF THE INVENTION

Figure 8:
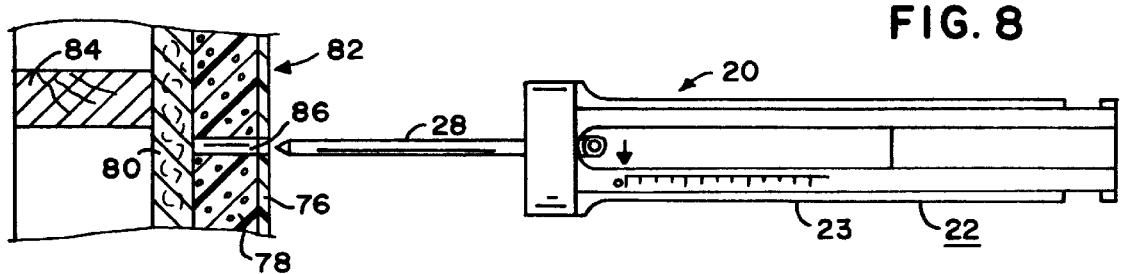
FIG. 8 is a view of the present invention before the pointed tip is inserted into a hole drilled within an outside wall of a building.
Figure 9:
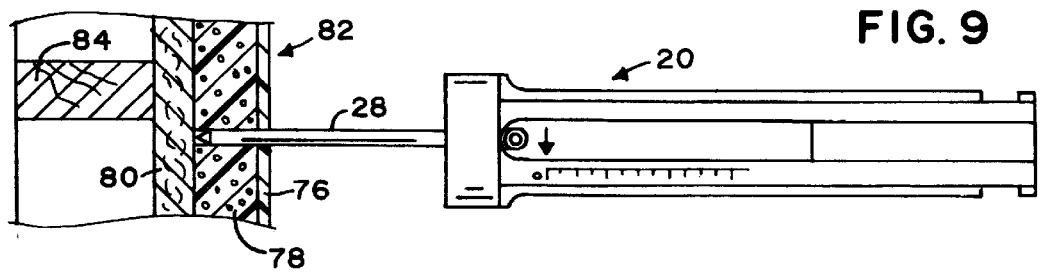
FIG. 9 is a view of the present invention after the pointed tip is inserted into a hole drilled within an outside wall of a building.

Referring to FIGS. 1–12, tester 20 comprises a casing 22 having an exterior grip 23 and having a cylindrical longitudinal bore 24 therethrough. A plug or piston 26 reciprocates within longitudinal bore 24, and tester 20 further has an elongated pointed tip 28 supported by casing 22 and threadedly received into piston 26 as by threads 30, and pointed tip 28 is thus mounted for mutual reciprocating movement together with piston 26, and its reciprocation is seen to be from an extended position as shown in FIGS. 1, 2, 8, 9, and 12, to a plurality of retracted positions toward casing 22 from said extended position, as, for example, those retracted positions shown in FIGS. 10 and 11. Cylindrical pointed tip 28 is preferably made of stainless steel for strength and endurance during repeated use.

Casing 22 is preferably constructed of well-known electrically-insulating high strength synthetic acetal resinous plastic sold by E.I. du Pont de Nemours and Company (1007 Market Street, Wilmington, Del.) under the trademark DELRIN so that pointed tip 28 is electrically insulated from the exterior grip 23. During use of the tester 20 in accordance with the method of the present invention as shown in FIGS. 8–12, it is possible that pointed tip 28 may inadvertently contact electrical wires (not shown) within the wall of the dwelling being tested, and the insulation of the exterior grip 23 from pointed tip 28 is provided so that the user of the tester 20 will not become electrocuted during such inadvertent contact of pointed tip 28 with electrical wires carrying lethal current.

A compression spring 36 is located within bore 24 of casing 22 rearward of piston 26, preferably received against the rear 38 of piston 26. Compression spring 36 is entrapped within bore 24 by a calibrating adjusting screw 40 that is threadedly received into the rear of bore 24. Calibrating adjusting screw 40 may have an axial hexagonal socket 42 as shown for receipt of a well-known allen wrench or, alternately and less preferably, may have a threaded slot (not shown) so that adjusting screw 40 may be advanced into or withdrawn from bore 24 in order to calibrate tester 20 to a particular compression spring 36. Spring 36 is thus seen to forcibly oppose movement of pointed tip 28 during reciprocation of pointed tip 28 from its extended position to the plurality of retracted positions of pointed tip 28. It has been found that a threaded slot can become "stripped" because of the grabbing grip of the threads of screw 40 by the DELRIN plastic used to construct casing 22, so a hexagonal socket 42 is preferred as shown. Preferably, compression spring 36 is selected and calibrated to a force of 16 pounds per inch (28 newtons per cm).

Pointed tip 28 is preferably 0.125 inches (3.175 mm) in diameter and has an exposed pointed end 32 that forms an inclusive angle 34 of 60 degrees. Angles for pointed end 32 other than 60 degrees have been tested but it has been found that an inclusive angle of 60 degrees produces the best results. It should be noted that different angles for pointed end 32 will produce different calibrations for the force seen by tester 20 during the testing of substrate for structural integrity. For example, if pointed end 32 were to be an inclusive angle of 180 degrees (i.e., a perfectly blunt end with a transverse cut), then the measured forces would be significantly higher than for a pointed end 32 having an inclusive angle of 60 degrees. Similarly, if pointed end 32 were to be a very small inclusive angle so that pointed tip 28 tapers very slowly toward pointed end 32, then the measured forces would be significantly lower than for a pointed end 32 having an inclusive angle of 60 degrees.

Tester 20 further has a scale 44 on casing 22 and an indicator 46 mounted for advancing movement with respect to scale 44. Scale 44 is calibrated in pounds (newtons) of force corresponding to the spring constant of spring 36, with the preferable calibration being 16 pounds per inch (28 newtons per cm). Indicator 46 is preferably mounted on a bowed plastic piece 48 that is slidably and frictionally received within a pair of opposed slots 50 within casing 22 for longitudinally reciprocating movement within slots 50. Plastic piece 48 preferably has 0.25 inch (6.4 mm) 45 degree chamfered corners 51 on its forward end 54. It shall be understood that the restorative bowing forces of plastic piece 48 causes plastic piece 48 to coact with slots 50 so as to frictionally restrain plastic piece 48 within slots 50. Plastic piece 48 has a forward-opening notch or slot 52 at its forward end 54 that receives and is engaged by post 56 that is threadedly received into and radially extends upward from piston 26. Post 56 reciprocates within a longitudinally-oriented slot 58 into bore 24 in response to mutual reciprocation of piston 26 and pointed tip 28, and causes indicator 46 to advancingly move with respect to scale 44 in response to inward reciprocation of pointed tip 28. However, the open forward end of forward-opening slot 52 of plastic piece 48 causes indicator 46 on plastic piece 48 only to advance along scale 44 during inward reciprocation of pointed tip 28, and the frictional forces between bowed plastic piece 48 and slots 50, together with the interaction of forward opening of slot 52 with post 56, are seen to together comprise holding means 60 for holding indicator 46 in its maximum advanced position during retrograde (i.e., outward) movement of pointed tip 28 toward its fully-extended position.

The forward end of tester 20 has a recessed circular cover plate 62 secured to casing 22 by screws 64. Cover plate 62 has a central axial bore 66 therethrough that acts as a guide for pointed tip 28.

Figure 12:
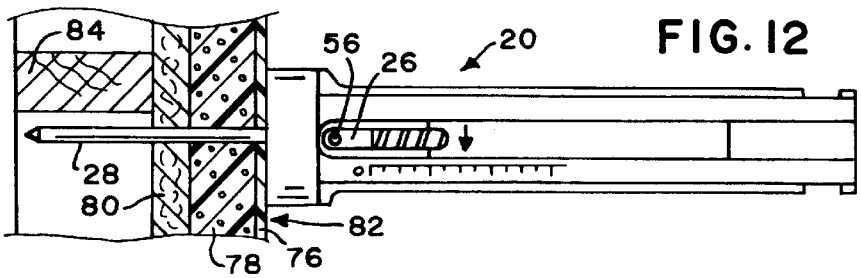
FIG. 12 is a view of the present invention against an outside wall of a building after testing a sample of rotten substrate behind synthetic stucco.

Interposed between the forward end 68 of piston 26 and the forward end 70 of longitudinal bore 24 is a rubber shock-absorbing washer 72 to absorb the shock of impact as piston 26 impacts the front of bore 24 when a structurally-weak substrate gives way during testing as shown in FIG. 12.

A pair of vertical and lateral slots 74 are provided at the rear of tester 20 for mounting tester 20 in a calibration fixture (not shown) during calibration of spring 36 using adjusting screw 40.

As hereinafter described, during testing of structural integrity of building materials such as, for example, a substrate such as a building's framing or sheathing, pointed tip 28 must first extend through any synthetic stucco cladding layer 76 (see FIGS. 9–11) and then through the insulating foamed plastic board 78 to reach the building material or sheathing substrate 80 that is to be tested for structural integrity. It should be understood that, while examples of using the invention are given herein to test the structural integrity of sheathing and framing beneath synthetic stucco and stucco, the use and application of the tester and method of the present invention is not so limited to merely testing substrate beneath synthetic stucco and stucco, because the present invention can be used to test the structural integrity of any building material as might be used, for example, in the framing or sheathing of a building that is suspected of rot or termite damage.

During the structural integrity test of substrate 80, pointed tip 28 must reciprocate a certain distance (determined by the spring constant of spring 36) in order to generate the necessary test forces in accordance with the method of the present invention. As hereinafter described, typical forces for acceptable structural integrity will be on the order of 28 pounds (124 newtons). For a spring constant of 16 pounds per inch of travel (28 newtons per cm), pointed tip 28 must reciprocate a distance of 1.75 inches (4.4 cm) (the "test reciprocation distance") following contact with substrate 80. In order to be able to reciprocate this test reciprocation distance after extending through the synthetic stucco cladding layer 76 and foamed plastic board 78, pointed tip 28 must extend out of tester 20 at least this test reciprocation distance plus the thickness of cladding layer 76 plus the thickness of foamed plastic board 78. For testing various force values of structural integrity up to 48 pounds (213.5 newtons) with the preferred spring having a spring constant of 16 pounds per inch of travel (28 newtons per cm), a maximum test reciprocation travel distance of three inches (7.6 cm) must be provided for pointed tip 28. Accordingly, various lengths of pointed tip 28 are provided to accommodate the varying thicknesses of foamed plastic board 78 and synthetic stucco cladding layer 76. Including and allowing for the 0.5 inch (1.27 cm) of threads 30 for receiving pointed tip 28 into piston 26 and approximately ⅝ inch (1.59 cm) of tip 28 extending through the front of tester 20 to piston 26, pointed tip 28 is preferably provided in end-to-end lengths (from pointed end 32 to the remote end of threads 30) of: 5.25 inches (13.3 cm) for synthetic stucco cladding and foamed plastic board thicknesses of about 1.0 inches (2.54 cm); 5.75 inches (14.6 cm) for synthetic stucco cladding and foamed plastic board thicknesses of about 1.5 inches (3.8 cm); and 6.25 inches (15.9 cm) for synthetic stucco cladding and foamed plastic board thicknesses of about 2.0 inches (5.1 cm).

Referring to FIGS. 8–12, the preferred method of the present invention can now be described in detail, using a building having synthetic stucco over sheathing as an example of an exterior building wall to be tested.

The wall 82 of a building to be tested, for example, typically has substrate sheathing comprising a plurality of wood studs 84 to which a sheathing 80 of gypsum board, oriented strand board ("OSB"), or 0.5 inch (1.27 cm) CDX plywood is attached. To this sheathing 80 is gluingly secured a typically 1.0 inch (2.54 cm) layer of insulating foamed plastic board 78 such as that sold under the trademark STYROFOAM. The synthetic stucco cladding layer 76 is applied atop the insulating foamed plastic board 78 in a manner heretofore discussed and well-known to those skilled in the art.

In order to perform a meaningful test of the structural integrity of the underlying sheathing 80, the particular type of sheathing (gypsum board, oriented strand board ("OSB"), or 0.5 inch (1.27 cm) CDX plywood, etc.) used on the building must be known so that the minimum resistance force for acceptable structural integrity can be used for comparison during subsequent testing of the building's sheathing. Accordingly, a test plug of approximately 4.0 inches by 4.0 inches (10 cm by 10 cm) in area of the synthetic stucco cladding layer 76 and foamed plastic board 78 is removed so as to expose the sheathing 80 in a dry, sheltered area of the wall so that the sheathing 80 can be examined in order to determine its type. Preferably this test plug will be removed in an unobtrusive location that will not be noticeable after the testing is completed.

After this test plug has been removed, reference should then be made to a chart of known acceptable values of resistive force resulting from using tester 20 on the particular type of substrate sheathing 80 when sheathing 80 is of known acceptable structural integrity (the "baseline substrate"), and the resulting value from the chart for the particular type of substrate sheathing becomes a baseline 1 value against which test results on the building can then be compared.

The tester 20 is then used, in a manner hereinafter described, to test the structural integrity of the underlying sheathing 80 at locations near the test plug. If the maximum resistive force measured at these test locations is within one pound (4.4 newtons) of the baseline value from the chart for acceptable structural integrity, then the structural integrity of the underlying sheathing 80 can be considered acceptable. Additional tests of substrate structural integrity can then be made at various locations and elevations around the building, in a manner hereinafter described.

To perform each test of substrate structural integrity, a hole 86 is first drilled through the synthetic stucco cladding layer 76 and foamed plastic board 78 to the underlying substrate sheathing 80, as shown in FIG. 8. Hole 86 should be slightly larger than the diameter of pointed tip 28 so as to allow the measured resistive forces sustained by pointed tip 28 penetrating into substrate 80 to be measured without interaction with stucco cladding layer 76 or foamed plastic board 78. The desired depth of hole 86 can be determined by measuring the total thickness of the stucco cladding layer 76 and foamed plastic board 78 at the previously-made test plug site hereinbefore described.

Figure 10:
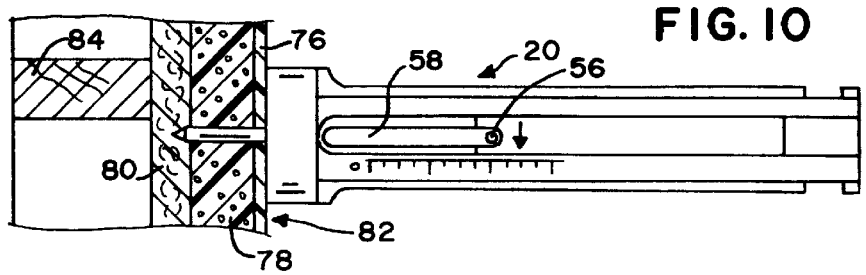
FIG. 10 is a view of the present invention forcibly pushed against an outside wall of a building so as to test a sample of marginally-acceptable substrate behind synthetic stucco.
Figure 11:
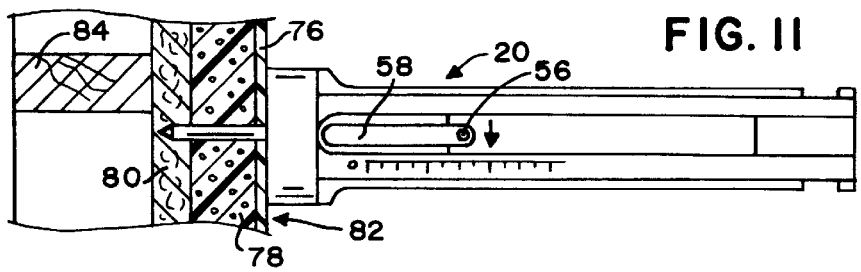
FIG. 11 is a view of the present invention forcibly pushed against an outside wall of a building so as to test a sample of unacceptably soft substrate behind synthetic stucco.

A pointed tip 28 of appropriate length for the depth of stucco cladding layer 76 and foamed plastic board 78 is then inserted into tester 20, and pointed tip 28 is then forcibly engaged with the portion of substrate 80 to be tested through hole 86 by forcing tester 20 against the outside of wall 82, and pointed tip 28 is thus caused to penetrate the portion of substrate 80 to be tested as shown in FIGS. 10 and 11.

Indicator 46 then measures and records the maximum resistive force sustained by pointed tip 28 against substrate 80 as pointed tip 28 is forcibly engaged therewith. The measured and recorded maximum resistive force is then compared against the acceptable value of resistive force for the baseline substrate having known acceptable structural integrity, and a determination is made as to the structural integrity of the tested portion of substrate 80. If the maximum resistive force measured during any given test is substantially below the acceptable baseline value, then the tested portion of substrate can be declared defective and unacceptable If the maximum resistive force measured during any given test is at least as great as the acceptable baseline value, then the tested portion of substrate can be declared to be of acceptable structural integrity.

At the conclusion of testing, the EIFS synthetic stucco cladding can be repaired where the test plug was removed and the test holes 86 can be filled with an appropriate sealant.

FIG. 10 shows the tester 20 forcibly pushed against outside wall 82 while testing a sample of marginally-acceptable substrate 80 behind synthetic stucco.

FIG. 11 shows the tester 20 forcibly pushed against outside wall 82 while testing a sample of unacceptably soft substrate 80 behind synthetic stucco.

FIG. 12 shows the tester 20 against an outside wall of a building after testing 47 a sample of rotten substrate 80 behind synthetic stucco.

A typical baseline value for gypsum sheathing 80 having acceptable structural integrity is 28 pounds (125 newtons). Soft and just barely-acceptable gypsum substrate 80 might have a maximum resistive force of 24 pounds, while unacceptable gypsum substrate might have a maximum resistive force of 22 pounds or less. The substrate 80 tested in FIG. 12 is clearly rotten and the pointed tip 28 has broken completely through the substrate 80. The shock-absorbing rubber washer 72 (see FIG. 2) absorbed the impact of piston 26 against the forward end 70 of bore 24 when pointed tip 28 broke through substrate 80 during the test shown in FIG. 12).

The tester of the present invention can also be used to test the structural integrity of various wood portions of a dwelling such as door frames, molding, window frames, etc., simply by using probe tips of slightly smaller diameter (preferably 1/64 inch (0.4 mm) smaller in diameter than the standard pointed tip discussed hereinbefore) and by providing calibrated baseline values for similar types of known-good wood. Harder woods (e.g., oak) will be understood to have correspondingly greater baseline values of minimum acceptable resistive force for acceptable structural integrity.

Although the present invention has been described and illustrated with respect to a preferred embodiment and a preferred use therefor, it is not to be so limited since modifications and changes can be made therein which are within the full intended scope of the invention.

I claim:

1. A tester for testing for structural integrity of a building material, said tester comprising:
    (a) a casing having an exterior grip;
    (b) an elongated pointed tip supported by said casing for reciprocation with respect thereto from an extended position and having an exposed pointed end extending remote from said casing, said pointed tip being electrically insulated from said exterior grip and being adapted to engage and penetrate a portion of building material to be tested;

(c) a spring forcibly opposing movement of said pointed tip with respect to said casing during said reciprocation of said pointed tip from said extended position toward said casing;

(d) a scale on said casing;

(e) an indicator mounted for advancing movement with respect to said scale and responsive to said reciprocation of said pointed tip from said extended position toward said casing; and (f) holding means for holding said indicator in its maximum advanced position during retrograde movement of said pointed tip toward said extended position;

said casing having a pair of opposed slots formed therein and said indicator being slidably and frictionally received within said slots.

2. A method of testing for structural integrity of a building material, said method comprising:

(a) providing a tester comprising:
 i. a casing;
 ii. an elongated pointed tip supported by said casing for reciprocation with respect thereto from an extended position and having an exposed pointed end extending remote from said casing, said pointed tip being adapted to engage and penetrate a portion of building material to be tested;
 iii. a spring forcibly opposing movement of said pointed tip with respect to said casing during said reciprocation of said pointed tip from said extended position toward said casing;
 iv. a scale on said casing;
 v. an indicator mounted for advancing movement with respect to said scale and responsive to said reciprocation of said pointed tip from said extended position toward said casing; and
 vi. holding means for holding said indicator in its maximum advanced position during retrograde movement of said pointed tip toward said extended position;
 said casing having a pair of opposed slots formed therein and said indicator being slidably and frictionally received within said slots:

(b) forcibly engaging said pointed tip with said portion of said substrate to be tested and causing said pointed tip to penetrate said portion of said building material to be tested;

(c) measuring a maximum resistive force sustained by said pointed tip against said portion of said building material as said pointed tip is forcibly engaged therewith;

(d) comparing said maximum resistive force against an acceptable value of resistive force for a baseline building material having known acceptable structural integrity.

3. The method of testing structural integrity of a building material as recited in claim 2, in which said method additionally comprises measuring said acceptable value of resistive force for said baseline building material having known acceptable structural integrity.

* * * * *